United States Patent [19]

Stiros

[11] 4,310,433
[45] Jan. 12, 1982

[54] SUPERFATTED LIQUID SOAP SKIN CLEANSING COMPOSITIONS

[75] Inventor: Paul Stiros, Maineville, Ohio

[73] Assignee: The Procter & Gamble Company, Cincinnati, Ohio

[21] Appl. No.: 183,125

[22] Filed: Sep. 2, 1980

[51] Int. Cl.$^3$ .................. C11D 9/26; C11D 9/48; C11D 17/08

[52] U.S. Cl. ............................... 252/132; 252/108; 252/122; 252/173; 252/367; 252/369; 252/DIG. 5; 252/DIG. 14

[58] Field of Search ............... 252/108, 132, 367, 368, 252/173, DIG. 14, DIG. 5, 122

[56] References Cited

U.S. PATENT DOCUMENTS

| | | | |
|---|---|---|---|
| 1,257,545 | 2/1918 | Starrels | 252/108 |
| 2,089,305 | 8/1937 | Stickdorn | 252/118 |
| 2,655,480 | 10/1953 | Spitzer et al. | 252/90 |
| 2,674,580 | 4/1954 | Henkin | 252/117 |
| 2,740,760 | 4/1956 | Pilch | 252/132 |
| 2,792,347 | 5/1957 | Stegemeyer | 252/108 |
| 2,792,347 | 5/1957 | Stegemeyer | 252/108 |
| 2,912,385 | 11/1959 | Golub | 252/132 |
| 2,980,629 | 4/1961 | Lambert | 252/369 |
| 3,361,213 | 1/1968 | Savins | 169/1 |
| 3,370,014 | 2/1968 | Reich et al. | 252/90 |
| 3,484,378 | 12/1969 | Reich | 252/90 |
| 3,503,887 | 3/1970 | Beebe | 252/108 |
| 3,553,138 | 1/1971 | Mace | 252/90 |
| 3,583,921 | 6/1971 | Healy | 252/90 |
| 3,953,351 | 4/1976 | Keller | 252/132 |
| 3,972,823 | 8/1976 | Howarth | 252/132 |
| 4,065,398 | 12/1977 | Brouwer | 252/108 |
| 4,190,549 | 2/1980 | Imamura | 252/132 |

FOREIGN PATENT DOCUMENTS 2847438  5/1980  Fed. Rep. of Germany.

OTHER PUBLICATIONS

*The Chemical Formulary* (Bennett) vol. 1, pp. 79, 80; vol. III, pp. 322, 323; vol. IV, p. 491; vol. V, p. 564; vol. VI, p. 448; vol. IX, p. 530; vol. XIX, p. 235; vol. XXI, p. 237; and vol. XXII, p. 30.

*Primary Examiner*—Dennis L. Albrecht
*Attorney, Agent, or Firm*—Ronald L. Hemingway; Richard C. Witte

[57] ABSTRACT

Clear, aqueous liquid skin cleansing compositions comprising saturated and unsaturated potassium soaps and free fatty acid.

4 Claims, No Drawings

SUPERFATTED LIQUID SOAP SKIN CLEANSING COMPOSITIONS

BACKGROUND OF THE INVENTION

This invention relates to liquid skin cleansing compositions. More particularly it relates to clear liquid skin cleansing compositions comprising soap and free fatty acid.

Although toilet bars comprise the most common form of skin cleansing agents, liquid skin cleansing products have recently been the subject of considerable interest in the trade. From the consumer's standpoint, liquids have advantages over toilet bars in that they avoid the problem of washstand messiness and they have the desirable feature of personalized use in that they can be dispensed in such a manner that each user of the product only comes into contact with that portion of the product which he or she actually uses.

In the formulation of soap-based toilet bar compositions it has been desirable to include free fatty acids in the composition. Such compositions are referred to as "superfatted" soaps. The free fatty acid contributes substantially to the lathering performance of the composition and also provides a mildness benefit in that it produces a lower pH product than is obtained with fully neutralized soap, and it has an emollient effect on the skin (See U.S. Pat. No. 3,576,749, Megson et al., issued Apr. 27, 1971).

Liquid soap-based skin cleansing products are well known in the art and generally use potassium neutralized fatty acids (See U.S. Pat. No. 2,912,385, Golub et al., issued Nov. 10, 1959). These have a higher solubility than the sodium soaps which are normally used in toilet bars. Free fatty acids can be incorporated into such compositions by using added solubility agents such as synthetic surfactants and/or hydrotropes.

Liquid soaps have been formulated with mixtures of saturated and unsaturated soaps to achieve highly concentrated, physically stable systems (See U.S. Pat. No. 4,065,398, Brouwer, issued Dec. 27, 1977, and U.S. Pat. No. 2,655,480, Spitzer et al., issued Oct. 13, 1953).

The object of the present invention is to provide concentrated clear aqueous skin cleansing compositions which comprise soap and free fatty acids, and which do not require the use of additional solubilizing agents.

SUMMARY OF THE INVENTION

The present invention comprises clear, aqueous, concentrated superfatted skin cleansing compositions which comprise potassium-neutralized and unneutralized fatty acids wherein said fatty acids comprise a mixture of saturated and unsaturated fatty acids.

DETAILED DESCRIPTION OF THE INVENTION

The present invention relates to aqueous liquid skin cleansing compositions which are based on superfatted soap. By utilizing the proper combination of saturated and unsaturated fatty acids in formulating said compositions they can be made in a clear, stable form without the use of synthetic detergents and/or hydrotropes.

The compositions herein comprise:

1. from about 5% to about 25% of a mixture of potassium-neutralized and unneutralized fatty acids, the weight ratio of neutralized to unneutralized fatty acids being from about 24:1 to about 7:1, the said fatty acids consisting essentially of $C_{12}$ to $C_{14}$ saturated fatty acids and $C_{16}$ to $C_{18}$ monounsaturated fatty acids, said fatty acids being present in a weight ratio of from about 1.2:1 to about 0.5:1 of saturated fatty acids to unsaturated fatty acids, and 2. from about 50% to about 94% water.

All percentages herein are "by weight" unless specified otherwise.

The saturated fatty acids utilized in the composition herein consist essentially of $C_{12}$ to $C_{14}$ chain lengths, i.e., lauric, tridecanoic and myristic acids. The lauric and myristic fatty acids can be obtained from synthetic sources, as well as from the hydrolysis of natural oils such as coconut oil and palm kernel oil. Tridecanoic acid is generally only available from synthetic sources. Completely pure saturated fatty acids of any particular chain length are very difficult to procure, and therefore it is contemplated within the present invention that the saturated fatty acids used herein can contain minor amounts of other fatty acids. For example, typical coconut oil fatty acids used as a source of $C_{12}$ and $C_{14}$ fatty acids will consist of about 15% $C_8$ to $C_{10}$ acids, about 48% $C_{12}$ acid, about 18% $C_{14}$ acid, about 9% $C_{16}$ acid, about 2% $C_{18}$ acid and about 8% $C_{18}$ unsaturated acids.

The unsaturated fatty acids used in the compositions herein consist essentially of $C_{16}$ and $C_{18}$ monounsaturated fatty acids, i.e., palmitoleic and oleic acid. The unsaturated fatty acid of choice is oleic acid because of its greater availability. Pure oleic acid is difficult to obtain; therefore, the oleic acid utilized in the compositions of the invention can be from a source such as commercial tallow-derived oleic acid which typically comprises about 3% myristoleic acid, about 6% palmitoleic acid, about 73% oleic acid, about 8% linoleic acid, about 3% linolenic acid and about 7% saturated acids. Vegetable-derived oleic acids, of course, can also be used.

The soaps of the compositions herein are potassium-neutralized soaps. These are obtained by neutralizing the fatty acids in the conventional manner utilizing an alkaline potassium salt such as potassium hydroxide or potassium carbonate. The compositions herein contain from about 5% to about 25% (preferably from about 15% to about 25%) of a mixture of potassium neutralized and unneutralized fatty acids. For purposes of describing the present invention, the amount of fatty acid in the compositions is expressed in terms of fatty acid, without regard to whether it is neutralized or unneutralized. For example, 10% of potassium-neutralized lauric acid (i.e., potassium laurate soap) is calculated, for purposes of describing the invention, as 8.4% lauric acid.

The ratio of neutralized to unneutralized fatty acids in the compositions herein is from about 24:1 to about 7:1, preferably from about 14:1 to 7:1. Fully neutralized potassium soap compositions, when measured as a 1% solution based on total fatty acids, have a pH of about 10.3. The compositions herein have a pH of from about 8.7 to 9.7 when measured on a 1% total fatty acids solution basis.

The total ratio of saturated $C_{12}$ to $C_{14}$ fatty acids to unsaturated $C_{16}$ to $C_{18}$ fatty acids in the compositions herein is from about 1.2:1 to about 0.5:1.

The compositions herein contain about 50% to about 94% water. The water is preferably soft or deionized water, since the presence of alkaline earth and heavy metal ions in water used to make the compositions herein can create insoluble soaps.

The compositions herein can contain synthetic detergents such as, for example, fatty alcohol sulfates, alkyl benzene sulfonates, fatty alcohol ethoxylates or fatty acid alkanol amides, but preferably the compositions herein are substantially free of synthetic detergents.

OPTIONAL COMPONENTS

The compositions herein can contain any of the usual optional materials included in soap formulations. These include, for example, perfumes, dyes and antimicrobial agents such as 3,4,4'-trichlorocarbanilide. Perfumes are used at levels of from about 0.1% to about 2.0%, dyes at levels of from about 2 ppm to about 1000 ppm and antimicrobials at levels of from about 0.1% to about 2.0%.

Conventional emollients can be incorporated into the compositions at levels of from about 1% to about 10%. Such materials include, for example, glycerine, mineral oils, paraffin wax, fatty sorbitan esters (See U.S. Pat. No. 3,988,255, Seiden, issued Oct. 26, 1976), lanolin and lanolin derivatives, esters such as isopropyl myristate and triglycerides such as coconut oil or hydrogenated tallow.

Although the compositions herein are inherently clear, agents which impart opacity or pearlescence can be added, if desired, at levels from about 0.1% to about 5.0%. These include, for example, latex compounds (e.g., the Lytrons® from Monsanto Company), fatty esters (e.g., ethylene glycol distearate from Emery Industries), microcrystalline cellulose (Avicel® from FMC Corporation) and synthetic silicates (e.g., Microcel® from Johns-Manville Co.).

The compositions herein can also contain viscosity adjusting agents, for example, salts such as sodium chloride, sodium sulfate, potassium chloride and potassium nitrate and organic thickeners such as polymers, gums, cellulosic derivatives and the like.

To increase the color, odor and microbial stability of the compositions herein, compounds such as antioxidants (BHA and BHT) sequestering agents (EDTA) and antimicrobial preservatives (Parabens® from Washine Chemical Corp.) may be added at levels of from about 10 ppm to about 5000 ppm.

The compositions herein are clear, homogeneous and physically stable at ordinary ambient temperatures (65°–90° F.). When cooled to very low temperatures (e.g., 30°–40° F.) they tend to become cloudy and non-homogeneous. However, upon warming back to ambient temperatures they again become clear, homogeneous and physically stable.

COMPOSITION PREPARATION

The compositions of the present invention are conveniently prepared by partially neutralizing a mixture of the specified saturated and unsaturated fatty acids to an end point which provides the desired ratio of soap to free fatty acid, and then diluting with water to achieve the desired concentration. Alternatively, fully neutralized soap can be prepared at the desired concentration in water and then blended with free fatty acid to achieve the desired composition.

The compositions herein can be packaged for use in plastic squeeze bottles, pump dispensing containers and the like for convenient dispensing of desired portions of the compositions for individual usage. The compositions herein can also be packaged in pressurized aerosol packages, particularly if it is desired to use them as shaving soaps.

The invention will be further illustrated by the following examples.

EXAMPLE I

The following ingredients are used to prepare a composition of the present invention:

| Ingredient | Wt. % |
|---|---|
| Lauric acid | 13.87 lbs. |
| Oleic acid | 11.83 |
| Potassium hydroxide (45%) | 12.64 |
| Distilled water | 62.30 |
| Ethylene glycol distearate | 1.10 |
| Glycerine | 3.30 |
| Potassium chloride | 4.40 |
| Perfume | 0.55 |
| Total | 109.99 |

The following preparative procedure is used.
1. Mix 12.64 lbs. of 45% KOH with 62.30 lbs. distilled water and heat to 160° F.
2. Premix and heat 11.83 lbs. lauric acid and 11.83 lbs. oleic acid to 150°–170° F.
3. Slowly add the heated fatty acid mixture to the potassium hydroxide solution with agitation.
4. Adjust the mix to neutral soap by adding more potassium hydroxide or fatty acid mix, as necessary. Neutralization is determined by titration for excess reactants.
5. The following ingredients are then added while continuing the mixing:
   a. 3.3 lbs. glycerine
   b. 2.04 lbs. lauric acid
   c. 1.1 lbs ethylene glycol distearate
   d. 4.4 lbs. potassium chloride
6. The mixture is then cooled to 100°–110° F. and 0.55 lbs. perfume is added.
7. Cooling is then continued to 75°–85° F.

The composition thus prepared has the following nominal formula:

| Ingredient | Wt. % |
|---|---|
| Potassium laurate/oleate soap | 25.0 |
| Free fatty acids | 1.85 |
| Potassium chloride | 4.0 |
| Glycerine | 3.0 |
| Ethylene glycol distearate | 1.0 |
| Perfume | 0.5 |
| Water and miscellaneous | 64.65 |
| Total | 100.00 |

The composition is stable and homogeneous. It crystallizes when cooled to 40° F. but recovers to a homogeneous state when warmed to 65°–75° F. The composition is clear if the ethylene glycol distearate opacifier is deleted.

What is claimed is:

1. Clear aqueous liquid skin cleansing composition comprising: (1) from about 5% to about 25% of a mixture of potassium-neutralized and unneutralized fatty acids, the weight ratio of neutralized to unneutralized fatty acids being from about 24:1 to 7:1, the said fatty acids consisting essentially of $C_{12}$ to $C_{14}$ saturated fatty acids and $C_{16}$ to $C_{18}$ monounsaturated fatty acids, said fatty acids being present in a weight ratio of from about 1.2:1 to about 0.5:1 of saturated fatty acids to unsaturated fatty acids, and (2) from about 50% to about 94% water.

2. The composition of claim 1 wherein the amount of said neutralized and unneutralized fatty acids is from about 15% to about 25%.

3. The composition of claim 2 wherein the ratio of neutralized to unneutralized fatty acids is from about 14:1 to about 7:1.

4. The composition of claim 3 wherein the saturated fatty acids consist essentially of $C_{12}$ fatty acid and wherein the monounsaturated fatty acids consist essentially of $C_{18}$ monounsaturated fatty acid.

* * * * *